United States Patent
Larsson et al.

(10) Patent No.: US 8,647,327 B2
(45) Date of Patent: Feb. 11, 2014

(54) TEST UNIT FOR WOUND DRAINAGE DRESSINGS

(75) Inventors: Michael Larsson, Zug (CH); Simon Furrer, Lucerne (CH)

(73) Assignee: Medela Holding AG, Baar (CH)

( * ) Notice: Subject to any disclaimer, the term of this patent is extended or adjusted under 35 U.S.C. 154(b) by 645 days.

(21) Appl. No.: 12/741,647

(22) PCT Filed: Nov. 4, 2008

(86) PCT No.: PCT/CH2008/000465
§ 371 (c)(1),
(2), (4) Date: May 6, 2010

(87) PCT Pub. No.: WO2009/059444
PCT Pub. Date: May 14, 2009

(65) Prior Publication Data
US 2010/0268197 A1    Oct. 21, 2010

(30) Foreign Application Priority Data
Nov. 8, 2007 (CH) ........................................ 1734/07

(51) Int. Cl.
*A61M 27/00* (2006.01)

(52) U.S. Cl.
USPC ............. 604/543; 604/35; 604/305; 604/306; 604/307; 604/308; 604/313; 604/317; 604/318; 604/319; 604/320; 604/321; 604/322; 604/323; 604/540; 604/541; 604/542; 604/902; 606/131

(58) Field of Classification Search
USPC ................................................ 604/540–544
See application file for complete search history.

(56) References Cited

U.S. PATENT DOCUMENTS

| | | |
|---|---|---|
| 6,182,956 B1 | 2/2001 | McMillan |
| 7,070,584 B2 | 7/2006 | Johnson et al. |
| 2002/0065494 A1 | 5/2002 | Lockwood et al. |
| 2008/0077091 A1* | 3/2008 | Mulligan ...................... 604/147 |

FOREIGN PATENT DOCUMENTS

| | | |
|---|---|---|
| DE | 29520960 | 7/1996 |
| EP | 0117351 | 9/1984 |
| EP | 0620720 | 10/1994 |

(Continued)

OTHER PUBLICATIONS

International Search Report for corresponding International Application No. PCT/CH2008/000465, dated Aug. 17, 2009.

(Continued)

*Primary Examiner* — Tatyana Zalukaeva
*Assistant Examiner* — Ilya Treyger
(74) *Attorney, Agent, or Firm* — McDonnell Boehnen Hulbert & Berghoff LLP

(57) ABSTRACT

The invention relates to a test unit for wound drainage coverings comprising: a base body with at least one cavity; at least one supply line that runs through the base body and which connects an outer side of the base body to the cavity; a surface of the base body that is embodied as a support surface for supporting wound coverings and the wound drainage coverings thereof and several channels that run through the base body, the channels connecting the cavities to the support surface. Low pressure can be produced in the cavity and the channels when the support surface is covered in an air-tight manner. As a result, wound drainage applications are tested in different ways using simple and economical means.

14 Claims, 19 Drawing Sheets

(56) References Cited

FOREIGN PATENT DOCUMENTS

| | | |
|---|---|---|
| EP | 1284777 | 2/2003 |
| GB | 2305610 | 4/1997 |
| GB | 2416909 | 2/2006 |
| GB | 2442132 | 3/2008 |
| JP | 2007-103609 | 4/2007 |
| SU | 1698904 | 12/1991 |
| WO | 94/20041 | 9/1994 |
| WO | 00/61333 | 10/2000 |
| WO | 03/086282 | 10/2003 |
| WO | 2005/099644 | 10/2005 |
| WO | 2006/046060 | 5/2006 |
| WO | 2006/052839 | 5/2006 |
| WO | 2006/056294 | 6/2006 |

OTHER PUBLICATIONS

Swiss Search Report for corresponding Swiss Patent Application No. 1734/07, dated Jul. 3, 2008.
International Preliminary Report on Patentability and Written Opinion for corresponding PCT Application No. PCT/CH2008/000465, dated Jun. 10, 2010.

* cited by examiner

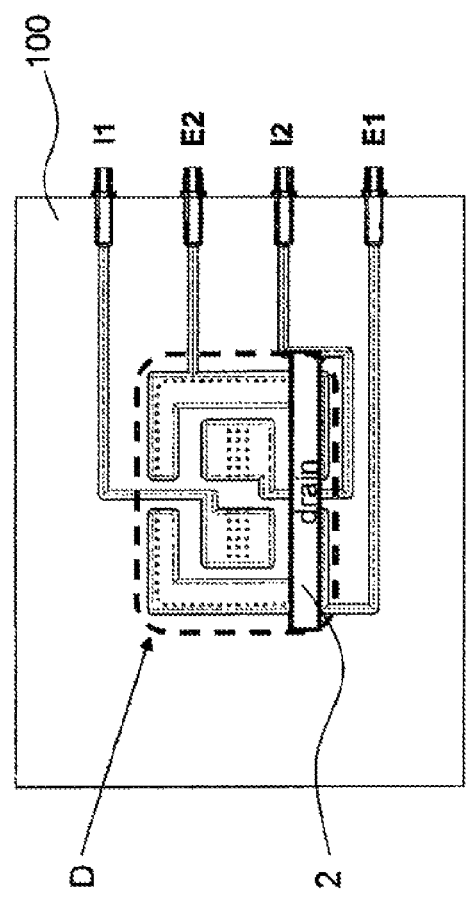
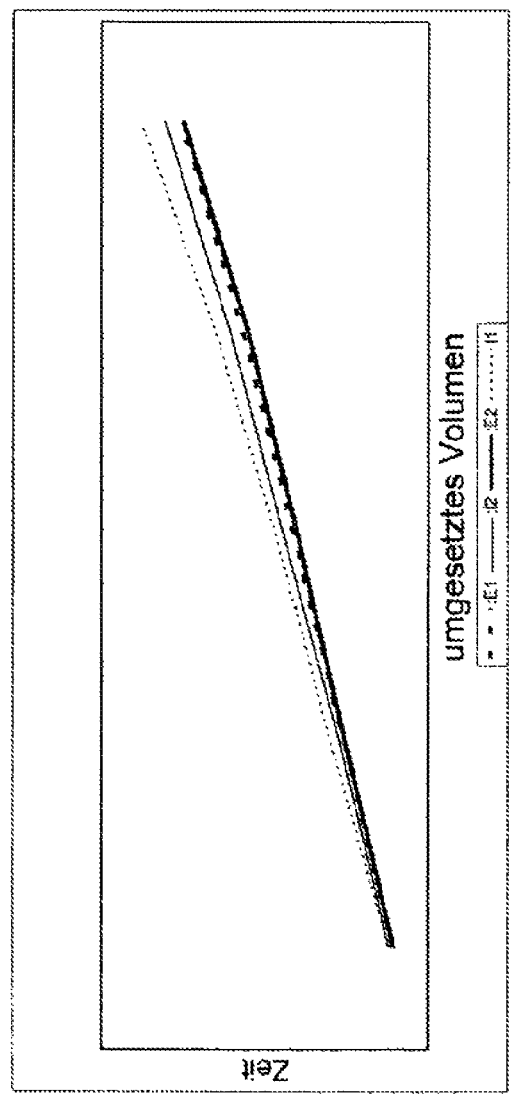
FIG. 8b
FIG. 8a

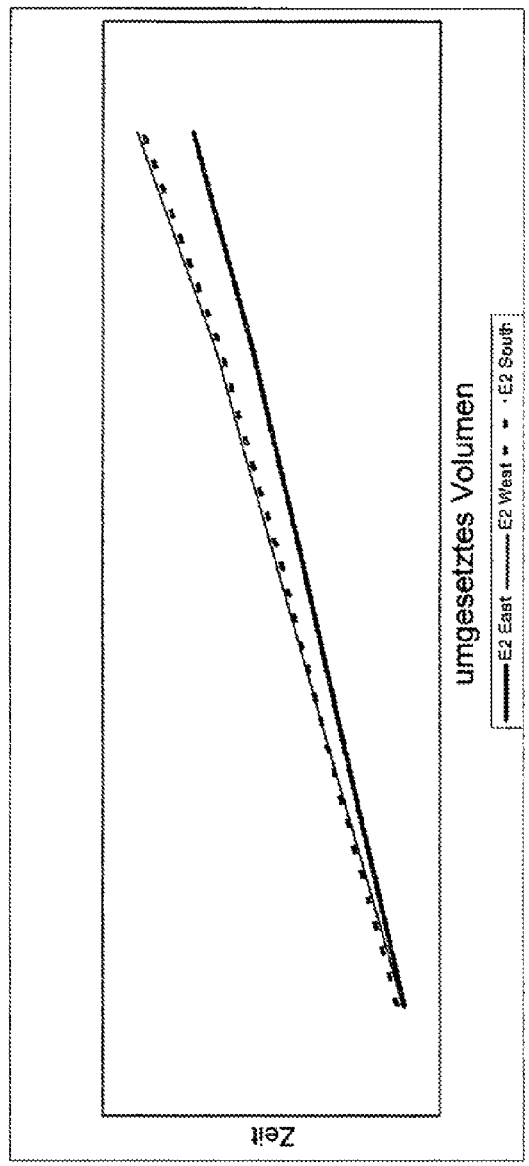
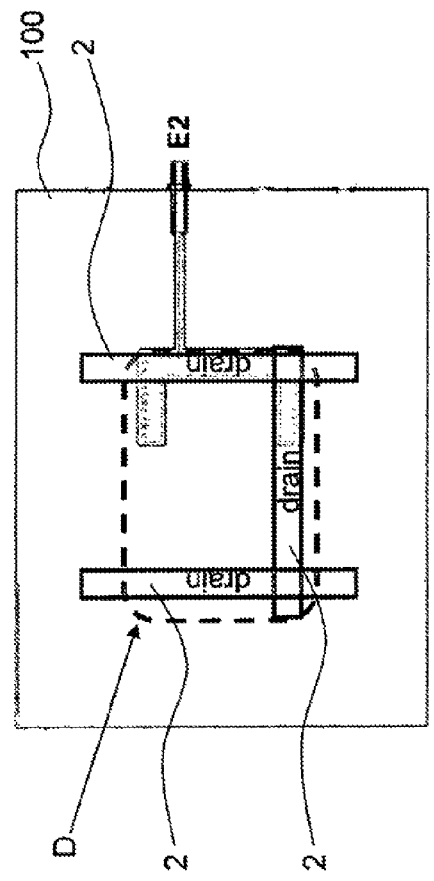
FIG. 10b
FIG. 10a

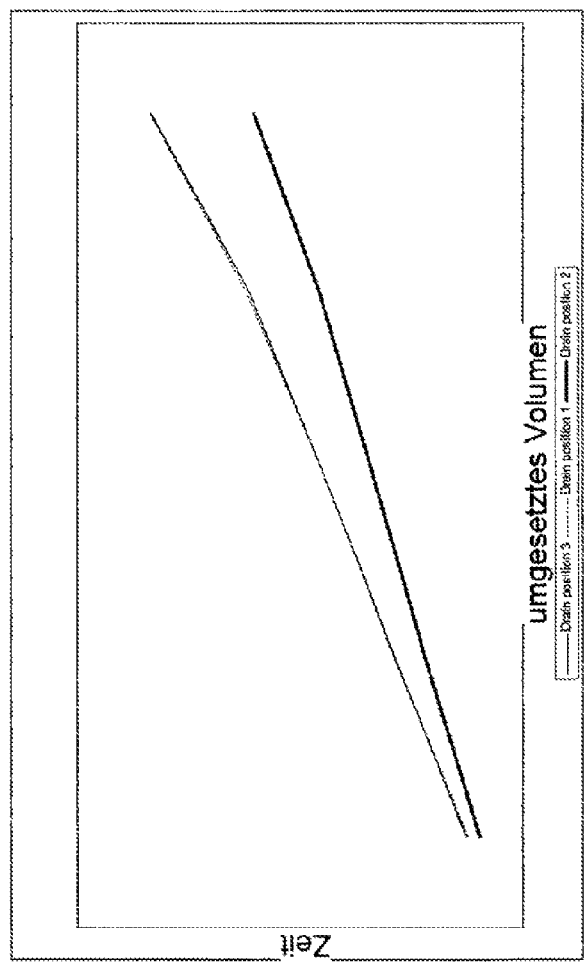
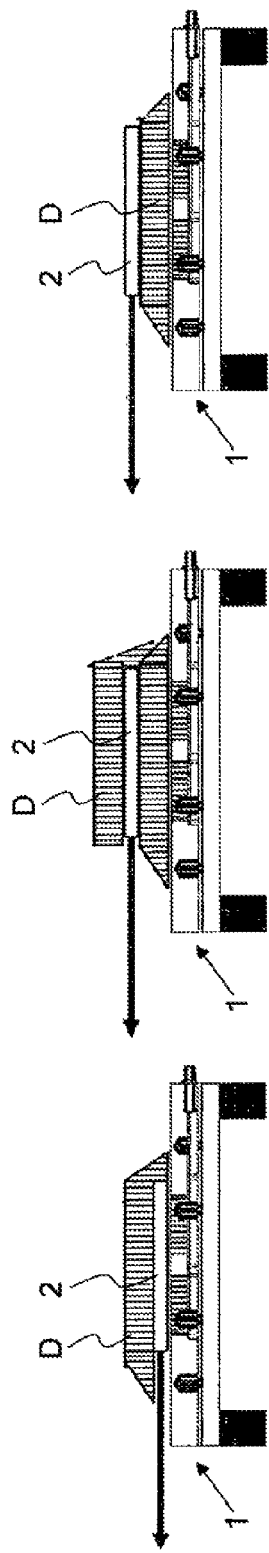
FIG. 14a  FIG. 14b  FIG. 14c  FIG. 14d

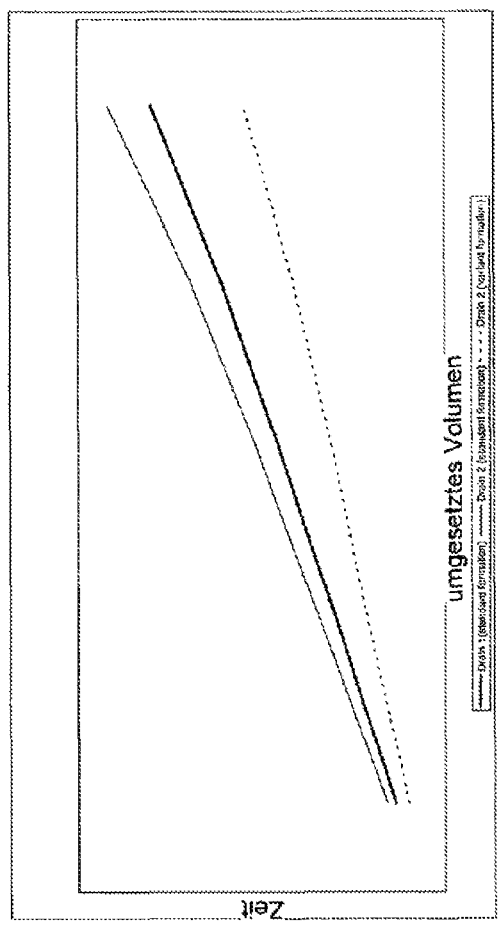
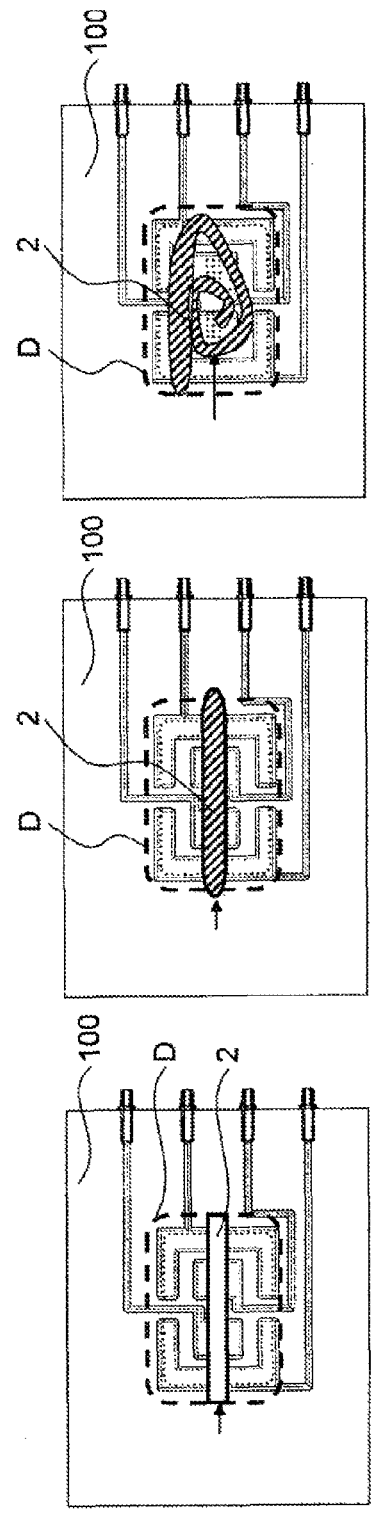
FIG. 15d
FIG. 15c
FIG. 15b
FIG. 15a

TEST UNIT FOR WOUND DRAINAGE DRESSINGS

CROSS REFERENCE TO RELATED APPLICATIONS

This application claims priority to International Application Serial No. PCT/CH2008/000465 filed Nov. 4, 2008, which claims priority to Swiss Patent Application No. 01734/07 filed Nov. 8, 2007, the contents of which are incorporated by reference herein in their entirety.

TECHNICAL FIELD

The invention relates to a test unit for wound drainage dressings.

PRIOR ART

It is known to treat large or poorly healing wounds using a vacuum drainage device. WO 94/20041, for example, describes this. A cover, for example a film or a stiff cap, is placed over the wound, such that a wound space is obtained. A drainage tube is inserted into the wound space from the outside and is connected to a suction pump in order to suck wound secretions out of the wound. In order to fill the wound space and, in particular, to distribute the vacuum uniformly across the surface of the wound, a wound dressing is placed on the wound. This wound dressing is usually composed of a foam insert with suitably configured pores. This foam insert can at the same time serve as an absorption body for the wound secretions.

Corresponding wound drainage dressings are known, for example, from WO 2006/056294, U.S. Pat. No. 7,070,584, EP 1 284 777 and EP 0 620 720. A wound drainage dressing with a foam insert outside the airtight top layer is described in WO 2006/052839. Wound drainage dressings of more complicated configuration are disclosed, for example, in WO 03/086232 and US 2002/0065494.

Many suggestions have therefore been made as to how wound drainage dressings of this kind could be configured. However, it is difficult to establish which wound drainage dressing is best used on which wound and with which suction pressure.

DISCLOSURE OF THE INVENTION

It is therefore an object of the invention to make available a device which permits uniform testing and optimized use of wound drainage dressings under conditions as close as possible to those encountered in practice.

The test unit according to the invention for wound drainage dressings comprises:
- a main body with at least one cavity,
- at least one supply line, which runs within the main body and which connects an outer face of the main body to the cavity,
- a surface of the main body, which surface is designed as a support surface for supporting wound drainage dressings and the covers thereof, and
- several channels, which run within the main body and which connect the cavity to the support surface,
wherein a vacuum is able to be generated in the cavity and the channels when the support surface is covered in an airtight manner.

The cavity and the channels simulate the wound. The cavity substantially simulates the wound bed, and the channels the pores in the wound floor.

Wound liquids of different compositions can be introduced into the simulated wound via the at least one supply line. It is possible to choose whether the wound liquid is supplied continuously, at predetermined time intervals or just once. The support surface permits easy and quick application of wound drainage dressings that are to be tested. These wound drainage dressings can be covered by an air-permeable, self-adhesive film, which is affixed to the support surface. However, they can also be used in the test unit along with the specific covers recommended by the manufacturer, for example rigid caps. In this case, the cap is simply affixed to the support surface, for example by means of an airtight, self-adhesive film.

The main body of the test unit preferably has a plane-parallel base plate, a supply plate and, arranged between these, a sealing plate, said supply plate having the channels and at least one recess for forming the cavity. The main body therefore has a relatively simple structure and can be produced inexpensively. It is also easy to clean, since the channels and the recess are easily accessible when the main body has been unscrewed.

Another advantage of the main body in this configuration is that several supply plates can be used with the same base plate and intermediate plate. In this way, the test unit is able to simulate a wide variety of sizes and arrangements of cavities and channels.

The test system according to the invention for wound drainage dressings has a test unit of this kind It further comprises at least one liquid reservoir, which is able to be connected to the at least one supply line, and a drainage container, which is able to be connected to the support surface via a vacuum line and a vacuum attachment.

The test system can be operated with a wide variety of suction pumps, in order also to take account of the effect of these suction pumps in the wound drainage. However, it is preferably used with a pump that comprises control and evaluation electronics or that can be connected to these. In this way, it is possible to control and document the degree of the applied vacuum, the duration of the applied vacuum, optionally any pressure changes or pulse sequences, and the supplied liquid. Of course, the volumetric flow and the flow rate of the suctioned drainage liquid are also measured and recorded and, if appropriate, additionally processed in the evaluation electronics.

The test unit according to the invention permits, among others, the following measurement possibilities:
- measuring the time that is needed, with the preselected vacuum, before a defined quantity of liquid is taken up by the wound drainage dressing being tested;
- measuring the different behavior of the wound drainage dressing at different vacuums (e.g. degree, pulse sequence, duration);
- comparing various liquids with different properties, for example water, secretion, blood, bacterially infected blood, acid or alkaline bacterial medium, saline solution;
- testing the different behavior of the wound drainage dressing by applying liquids to sectors of the test unit;
- testing the different behavior and the different degree of saturation of the wound drainage dressing in its individual zones, e.g. from the edge to the center.

The test unit according to the invention and the test system thus permit uniform testing of known wound drainage dressings. They permit more optimized use of these wound drainage dressings. Moreover, they are an important aid in the development of new wound drainage dressings and covers and also in the development of new suction pumps and new methods of wound drainage.

Other advantageous embodiments are set forth in the dependent claims.

BRIEF DESCRIPTION OF THE DRAWINGS

The subject matter of the invention is explained below on the basis of preferred illustrative embodiments and with reference to the attached drawings, in which:

FIG. 8a shows a view of the test unit in a third application;

FIG. 8b shows a graph of the measured volumetric values of the third application;

FIG. 10a shows a view of the test unit in a fifth application;

FIG. 10b shows a graph of the measured volumetric values of the fifth application;

FIG. 14a shows a view of the test unit in a first arrangement of the wound cover;

FIG. 14b shows a view of the test unit in a second arrangement of the wound cover;

FIG. 14c shows a view of the test unit in a third arrangement of the wound cover;

FIG. 14d shows a graph of the volumetric values measured according to the three arrangements in FIGS. 14a to 14c;

FIG. 15a shows a view of the test unit with a suction bar in a first form;

FIG. 15b shows a view of the test unit with a suction bar in a second form;

FIG. 15c shows a view of the test unit with a suction bar in a third form, and

FIG. 15d shows a graph of the volumetric values measured according to the three arrangements in FIGS. 15a to 15c.

DETAILED DESCRIPTION

Figure 1:
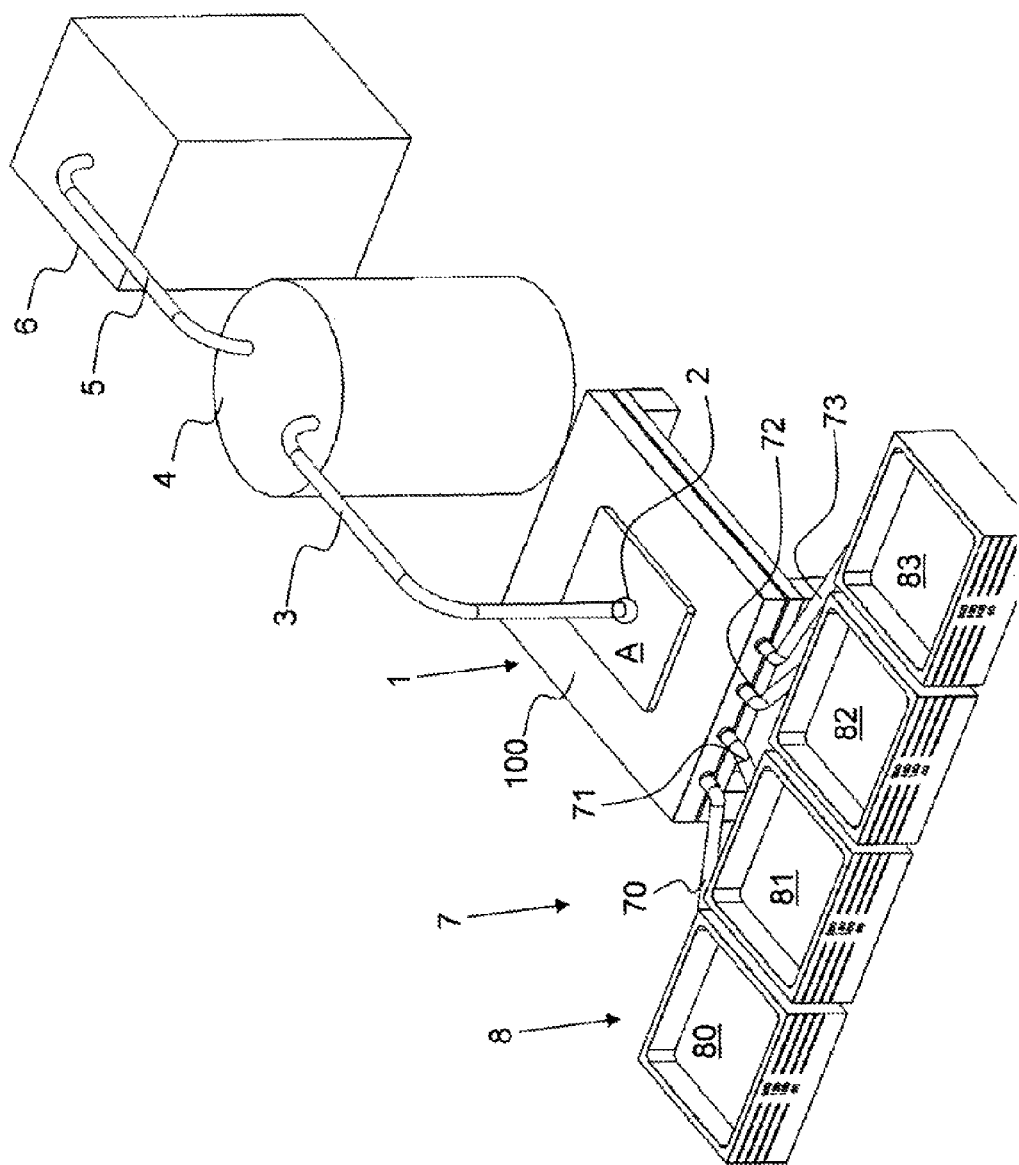
FIG. 1 shows a schematic representation of a test system according to the invention.

FIG. 1 shows a schematic representation of a test system according to the invention. It has a main body 1 of a test unit, a vacuum attachment 2, which is arranged on the main body 1 or can be connected thereto in an airtight manner via a wound cover A, a drainage line 3 connected to the vacuum attachment 2, a drainage container 4, into which the drainage line 3 opens, a pump line 5 leading from the drainage container 4, and a suction pump 6 connected to the pump line 5.

Figure 2:
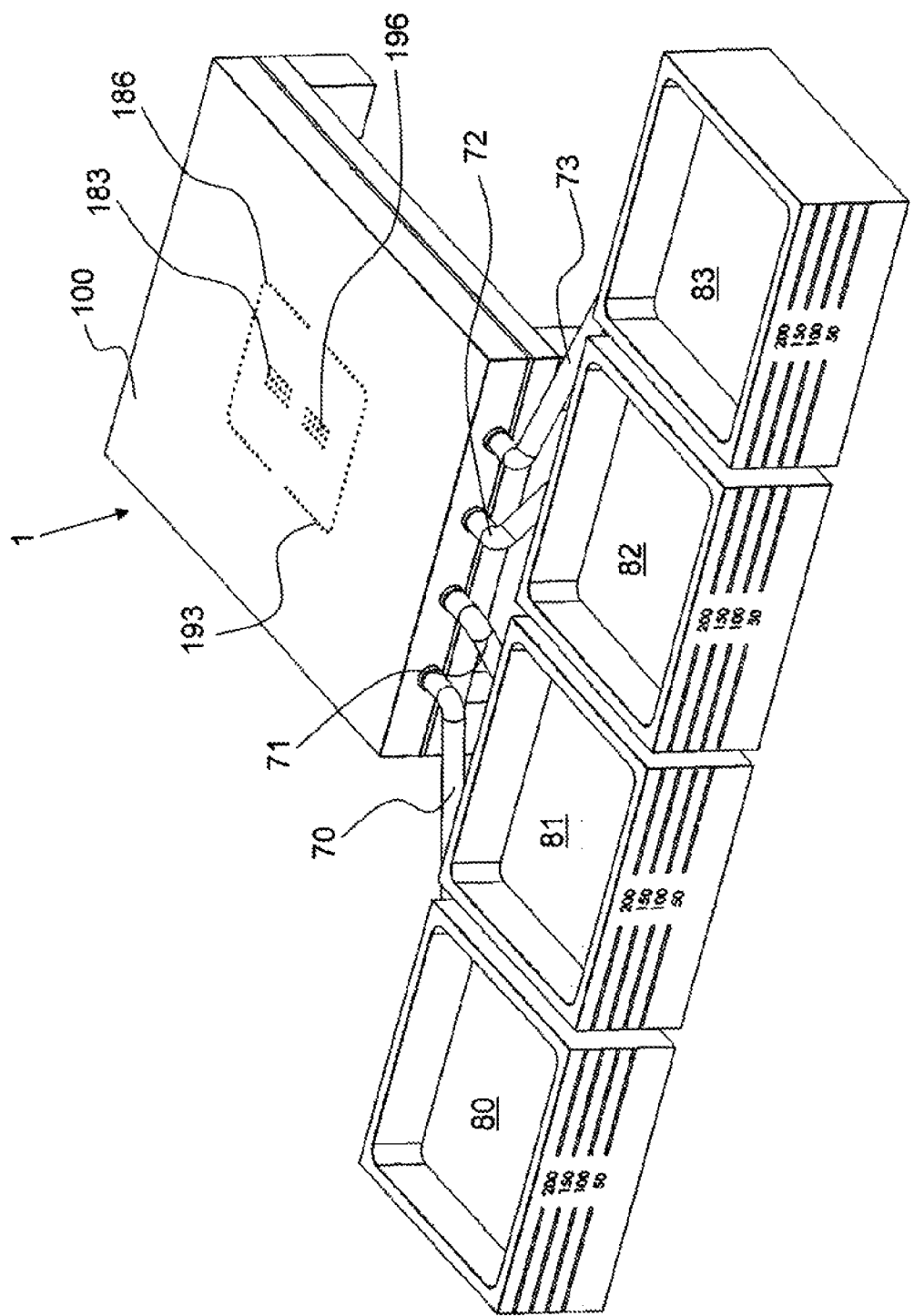
FIG. 2 shows a detail according to FIG. 1, with test unit and liquid reservoir system.

The main body 1 is also connected to a liquid reservoir system 8 via a connecting line system 7, which has at least one connecting line 70, 71, 72, 73. This liquid reservoir system 8 has at least one liquid reservoir 80, 81, 82, 83. The reservoirs 80, 81, 82, 83 preferably have a level indicator, as can be seen in FIG. 2.

The main body 1 has (see FIGS. 1 and 2) a support surface 100, which is preferably flat and has several channels 183, 186, 193, 196 leading into the interior of the main body 1. A wound dressing D that is to be tested can be placed on this support surface 100 and cover at least some of the channels 183, 186, 193, 196, and it can be covered by a standard wound cover A or by a wound cover A that is to be tested, and both are connected tightly to the vacuum attachment and to the main body 1. A self-adhesive film is preferably used for this purpose.

Figure 3:
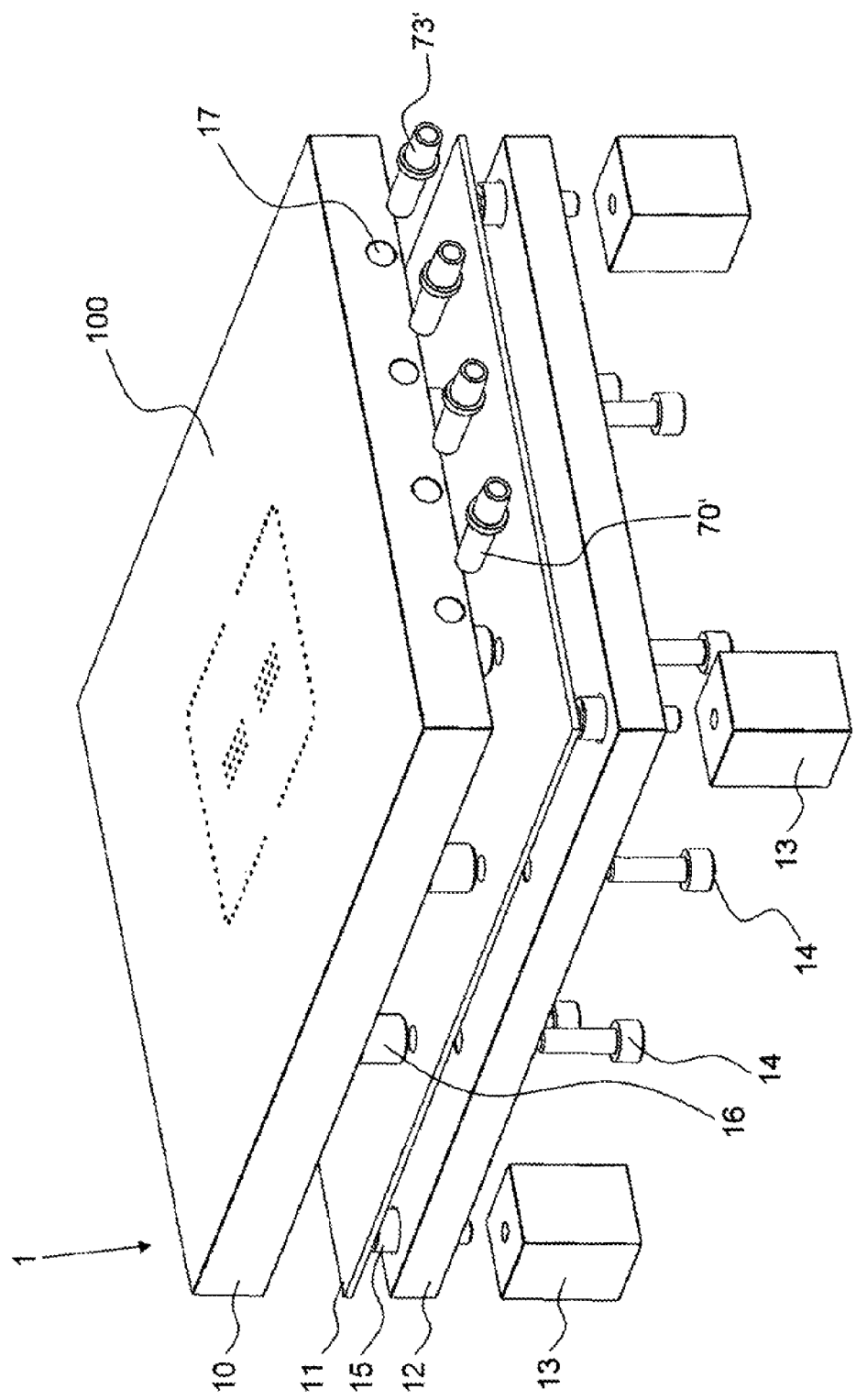
FIG. 3 shows an exploded view of the test unit according to FIG. 1.
Figure 4:
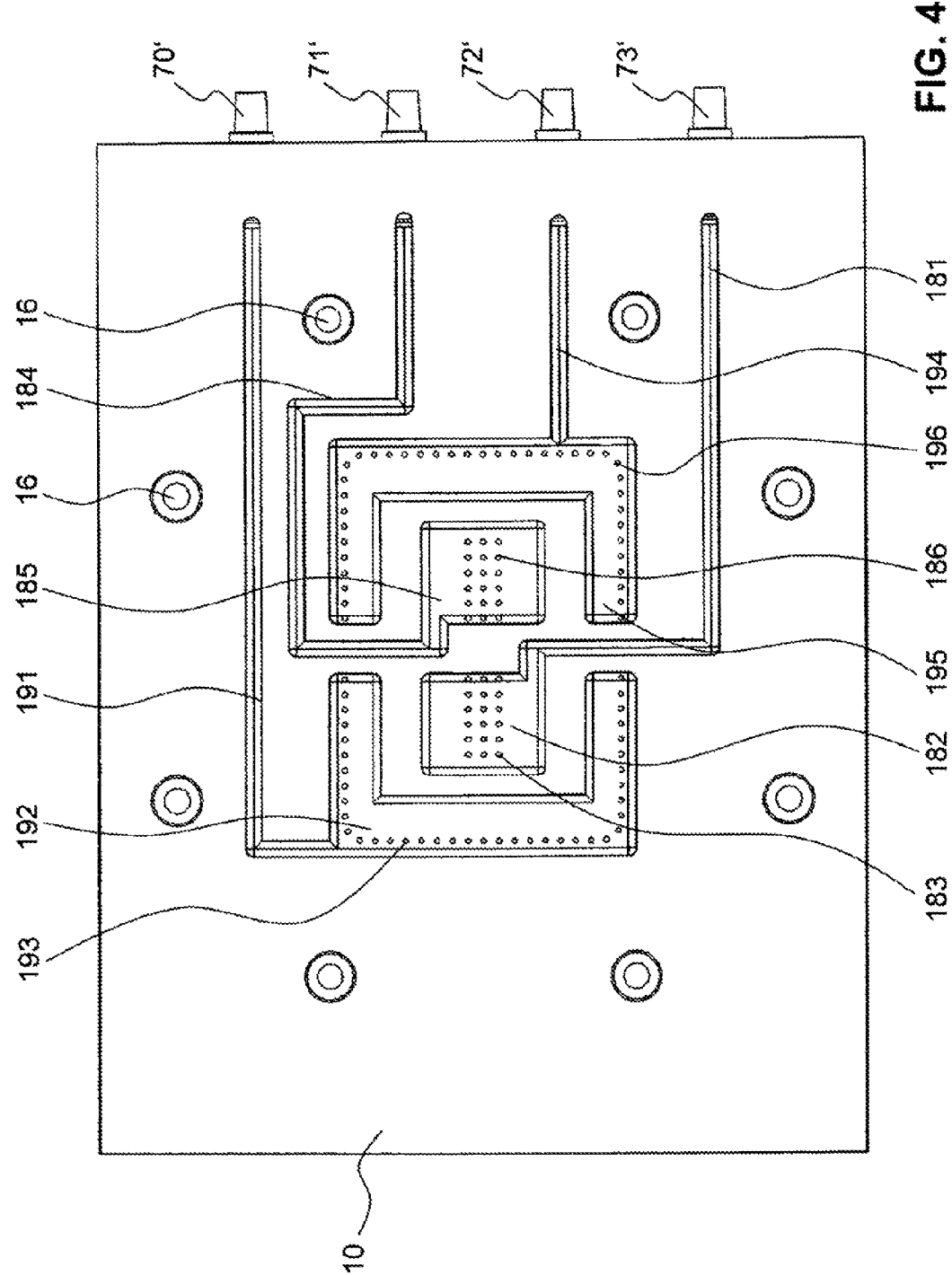
FIG. 4 shows a bottom view of a supply plate of the test unit.
Figure 5:
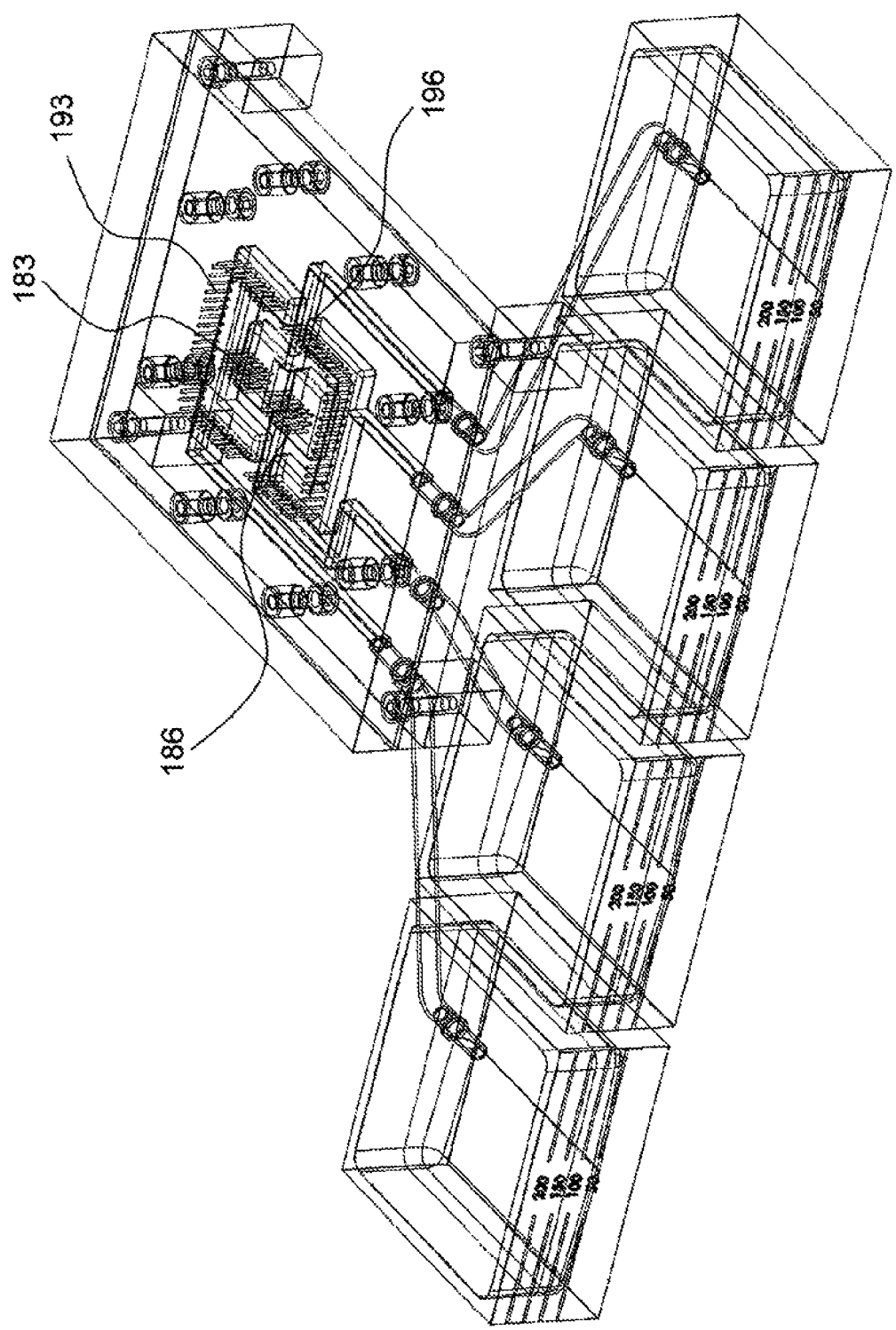
FIG. 5 shows an exploded view of the test unit and of the liquid reservoir system according to FIG. 2.

The main body 1 of the test unit is shown in more detail in FIGS. 3 to 5. It has a preferably plane-parallel base plate 12, a supply plate 10 and, arranged between these, a sealing plate 11. The base plate 12 and the supply plate 10 are preferably made of a plastic, in particular Plexiglas, or of a metal, in particular steel or aluminum. The sealing plate 11 is preferably made of a flexible sealing material, in particular silicone or rubber.

The sealing plate 11 is likewise preferably plane-parallel and has through-openings. Connecting screws 14 are guided through these openings in order to screw the base plate 12 to the supply plate 10 in an airtight and liquid-tight manner. For this purpose, threaded holes are provided in the supply plate 10, or threaded bushings 16 are let into the supply plate 10 flush with the lower surface thereof.

The base plate 12 preferably stands on feet 13, which likewise can be screwed, for example, to the base plate 12 via fastening screws 15.

The base plate 12 preferably has no elevations or depressions other than those for connection to feet 13 and to supply plate 10, nor does it have any inner bores or channels. The supply plate 10 is preferably also plane-parallel and has the same shape and surface area as the base plate 12. Both preferably comprise a generally rectangular shape. However, the supply plate 10 has recesses and bores.

As can be seen from FIG. 3, the supply plate 10 has bores at least on one end face, preferably specifically on one end face, which bores form supply openings 17 of the supply lines 181, 184, 191, 194 that can be seen in FIGS. 4 and 5. The abovementioned connecting lines 70, 71, 72, 73 open into these supply openings 17. For this purpose, attachment pieces 70', 71', 72', 73' are preferably present, which can be plugged into the openings 17.

According to the invention, the supply plate 10 has recesses which are closed at the top toward the support surface 100, except for the channels described below, and are open at the bottom toward the sealing plate 11 and base plate 12. These recesses are closed by the sealing plate 11 and the base plate 12 to form cavities 182, 185, 192, 195 completely separate from one another. They can have a wide variety of shapes. In the example shown here, a first cavity 182 and second cavity 185 have a constant rectangular longitudinal section and are adjacent to each other but spaced apart from each other. They here have the same surface area and preferably also the same depth, such that they have the same volume. A third cavity 192 and fourth cavity 195 are each designed so as to be spaced apart from and partially frame one of the first and second cavities 182, 185, respectively. For this purpose, they have a C-shaped longitudinal section, which is again preferably constant. They too preferably have the same volume. However, these cavities can also have other shapes and volumes. It is also possible for more or fewer than these four cavities to the present. They can together have a geometric pattern or have another arrangement in the supply plate 10. Moreover, they can have different depths in relation to the support surface 100 inside the supply plate 10.

These recesses are open toward the outside via the above-mentioned supply lines 181, 184, 191, 194. These supply lines 181, 184, 191, 194 are also formed in the supply plate 10 by grooves that are open at the bottom and that merge into closed tubes only in the end-face edge area. These grooves are tightly closed off by virtue of the sealing plate 11 and the base plate 12, except for the supply openings 17. Since no cavities have to be formed and no bores have to be established, the production of the supply plate is made easier and it is also easier to clean.

These supply lines 181, 184, 191, 194 can be of the same length or of different lengths. They preferably extend parallel to the support surface 100, such that the supply of liquid takes place parallel to the surface of the wound dressing. Each supply line preferably leads to a respective cavity and each supply line to a respective supply opening. However, they can also branch and serve several cavities, or a cavity can have several supply lines. All the supply lines preferably have the same internal diameter. However, they can also have different diameters.

From the cavities 182, 185, 192, 195, capillaries or channels 183, 186, 193, 196 lead outward to the support surface 100. Each cavity has several such channels. The channels of the same cavity can have the same internal diameter or different internal diameters. Similarly, channels of different cavities can have the same diameter or different diameters. They preferably extend in a direction perpendicular to the support surface 100, although they can also extend at an angle thereto. The channels of a cavity preferably form, on the support surface, a geometric pattern, and the latter can be differently configured for each cavity. The channels are preferably distributed as uniformly as possible across the surface area or at least over an area of the respective cavity.

The cavities preferably have a volume of 2 $cm^3$ to 4 $cm^3$. The channels are preferably 3 mm to 8 mm long and have an internal diameter of preferably 1 mm to 1.5 mm. The supply lines preferably have an internal diameter of 2 mm to 4 mm.

In a preferred embodiment, the test unit is heatable, such that the temperatures of the patient can be simulated.

By virtue of this test unit and this test system, it is now possible to test drainage applications. Thus, different test liquids can be introduced in a targeted manner from the liquid reservoirs into individual cavities. These test liquids can simulate wound liquids or treatment liquids.

Different wound dressings can be placed on the support surface and can be covered with different wound covers. Moreover, differently designed vacuum attachments (drains) can be used, which can also be arranged at different locations in relation to the wound dressing and to the filled cavities. By virtue of cavities of different shapes and different sizes, it is possible to simulate different types of wound bed. Moreover, the behavior of the same wound dressings, wound covers and drains can be tested with different suction pumps, different vacuums, suction sequences and different drainage duration.

Figure 6B:
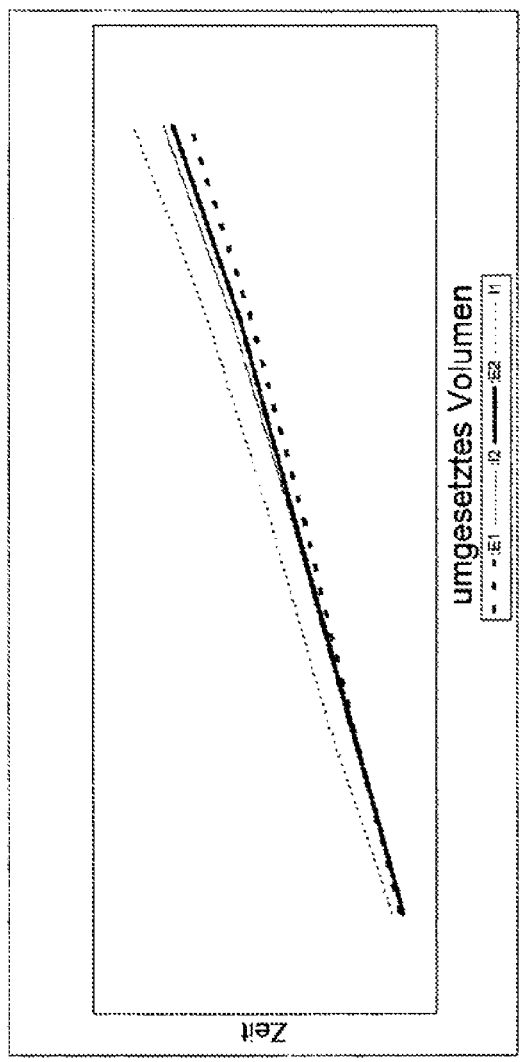
FIG. 6b shows a graph of the measured volumetric values of the first application.
Figure 6A:
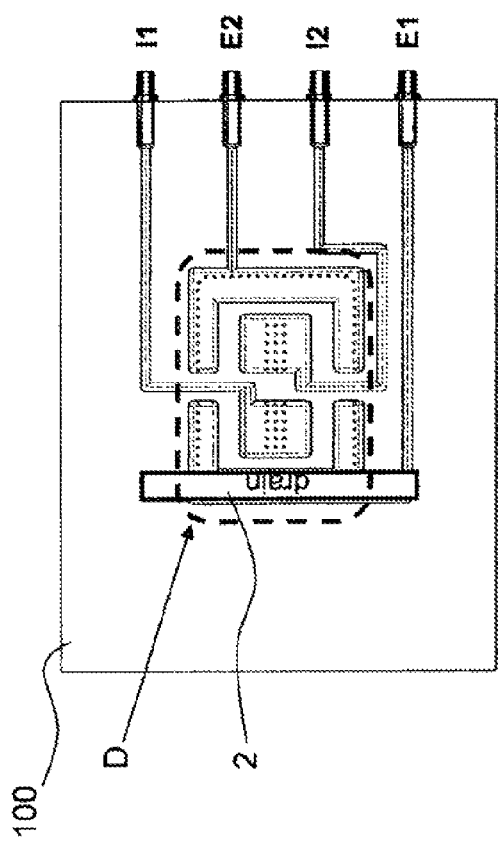
FIG. 6a shows a view of the test unit in a first application.

Such applications are shown in the figures described below. These are to be understood only as examples and are not exhaustive:

FIG. 6a shows a vacuum attachment (drain) 2 in the form of a rectangular bar which has a plurality of suction openings distributed uniformly along the length thereof and which is arranged over a rectangular wound dressing D. This wound dressing D covers the entire channel area of the support surface 100. The same wound liquid is supplied to the four cavities in succession via all of the supply openings, here designated as E1, E2, I1 and I2. In this example, no further liquid is supplied during the suction procedure. In other examples, however, this would be possible. Each individual supply is subjected to a vacuum and the flow behavior is measured. For all four cavities in succession, the same suction sequence is used (i.e., among other things, duration, degree of vacuum, possible variations in the pressure during the suction procedure).

FIG. 6b shows the measured values. The y-axis shows the time, the x-axis shows the volume converted during the suction. This volume is preferably measured in the drainage container. As can be seen, therefore, the distance at which the drain 2 is arranged from the suctioned cavity has an important role.

Figure 7B:
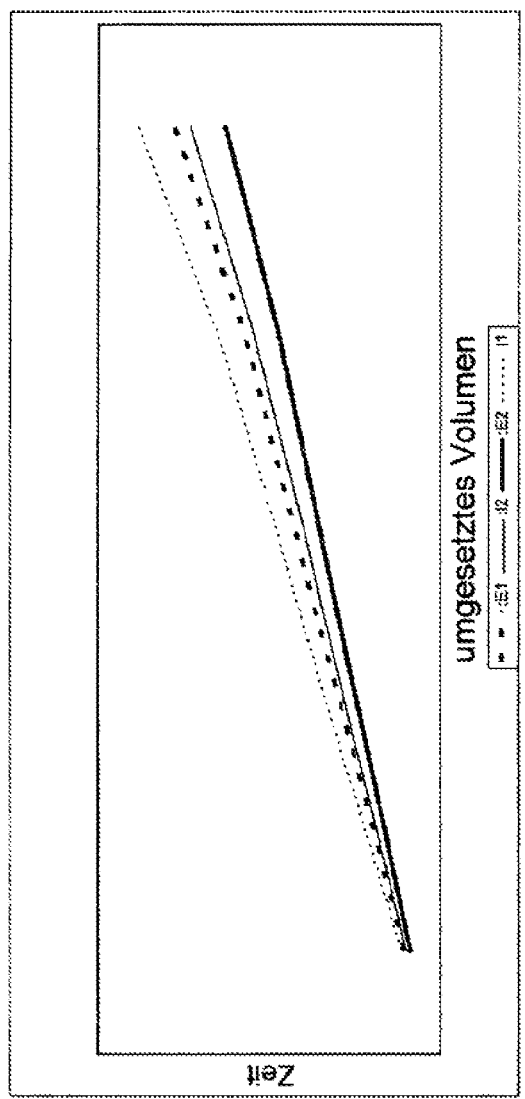
FIG. 7b shows a graph of the measured volumetric values of the second application.
Figure 7A:
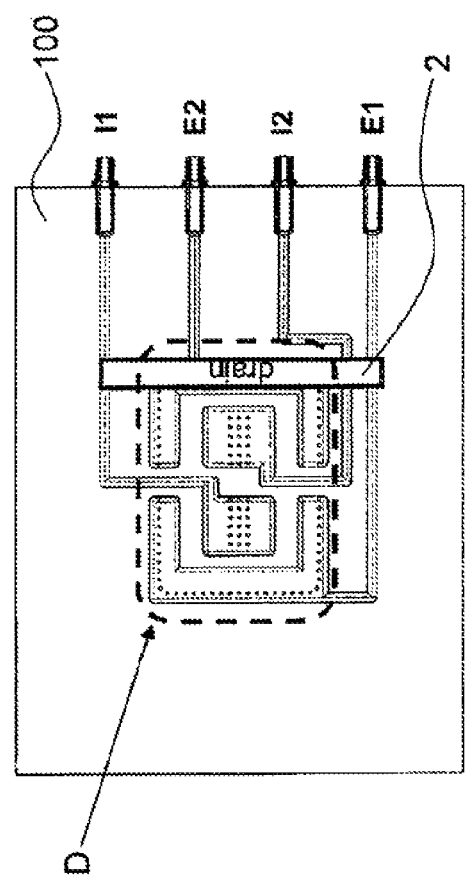
FIG. 7a shows a view of the test unit in a second application.

The same procedure was followed in FIG. 7a, and the same drain 2, the same wound dressing D and the same test liquid were used. Here, the drain 2 was arranged at the opposite end of the hollow chambers.

The measured values were again plotted in FIG. 7b.

The same procedure was again followed in the example according to FIGS. 8a and 8b. Here, the drain 2 is arranged in the lower area.

Figure 9B:
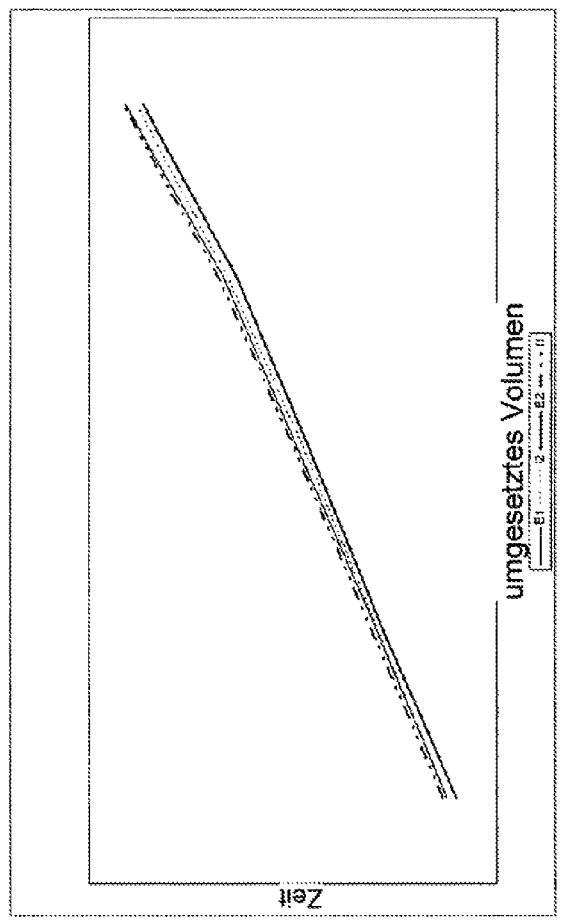
FIG. 9b shows a graph of the measured volumetric values of the fourth application.
Figure 9A:
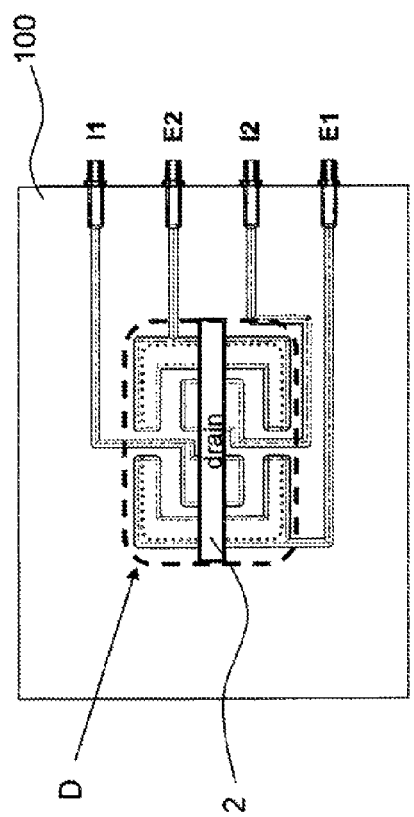
FIG. 9a shows a view of the test unit in a fourth application.

In the example according to FIGS. 9a and 9b, it will be seen that with the same procedure as in the other examples, but with the drain 2 placed across the center of the hollow chambers, the least variation occurs in the behavior of the four hollow chambers. Therefore, in the figures that follow, this arrangement is once again used in order to vary other parameters.

Figure 9C:
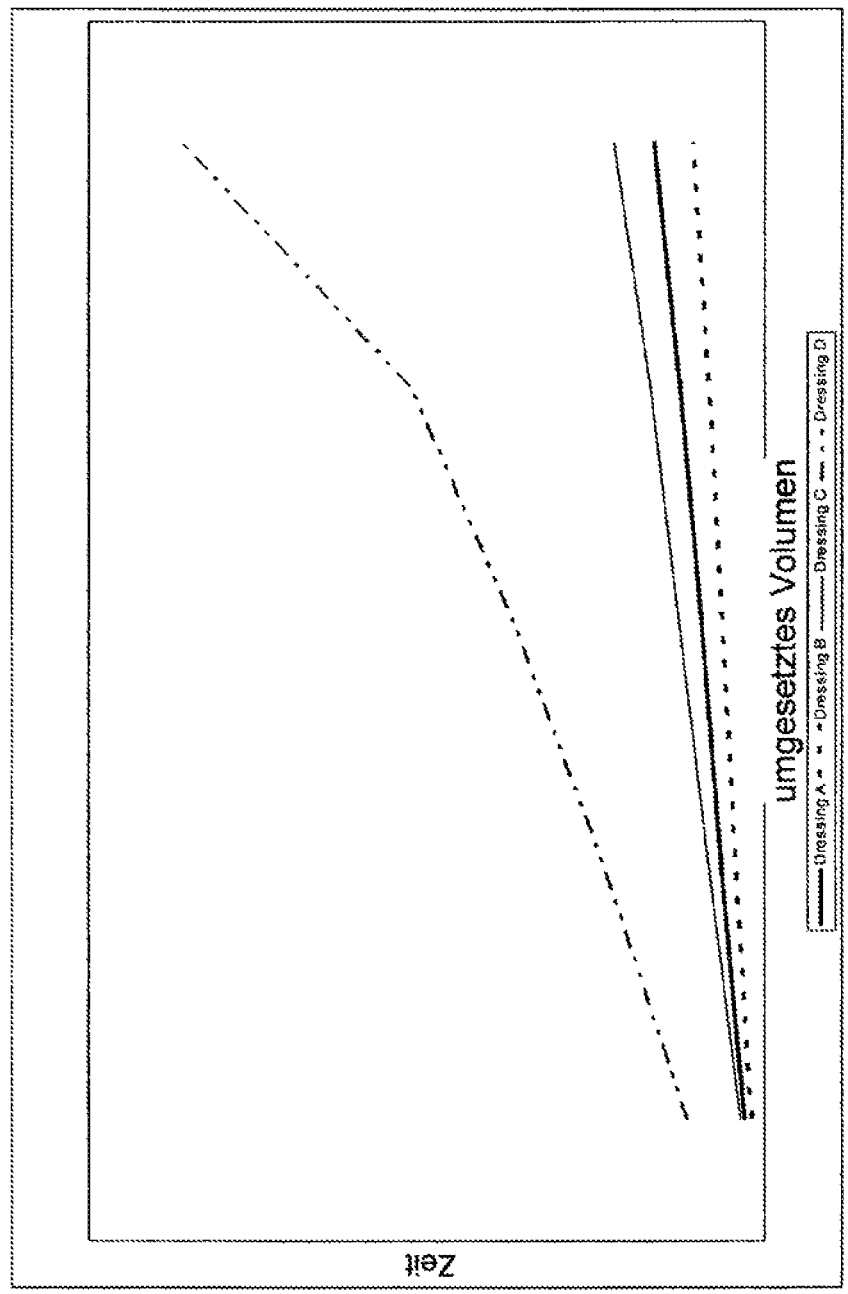
FIG. 9c shows a graph of the volumetric values measured when using different wound covers.
Figure 9D:
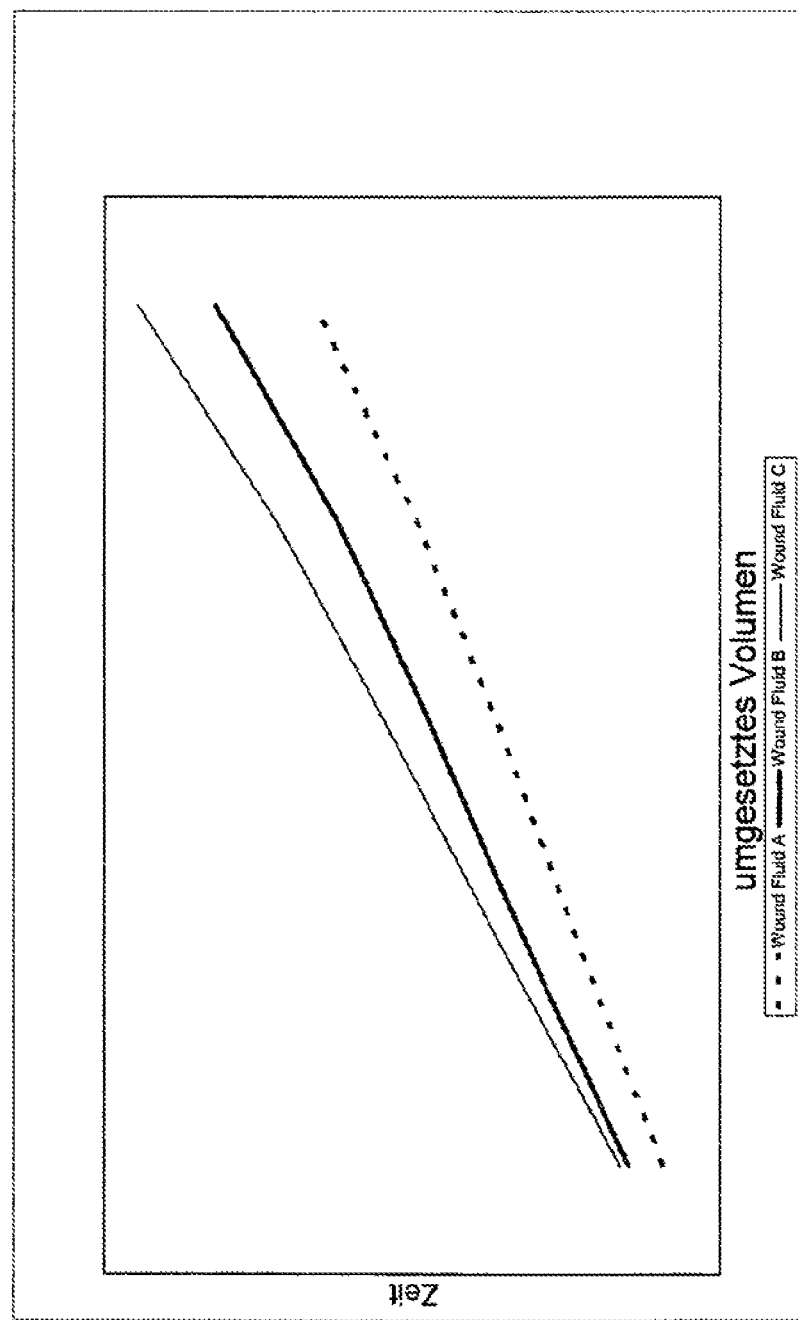
FIG. 9d shows a graph of the volumetric values measured when using different wound liquids.
Figure 9E:
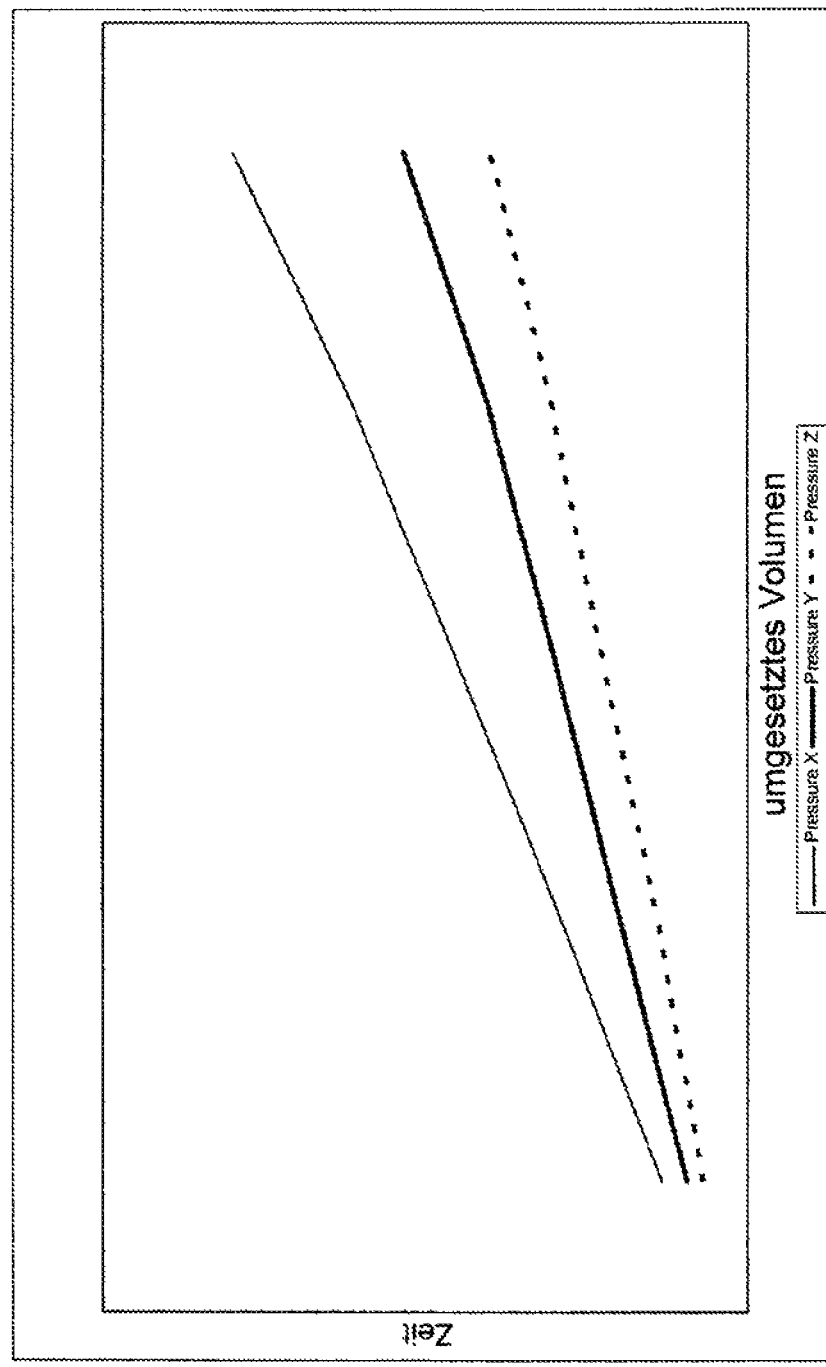
FIG. 9e shows a graph of the volumetric values measured when using different vacuums.
Figure 9F:
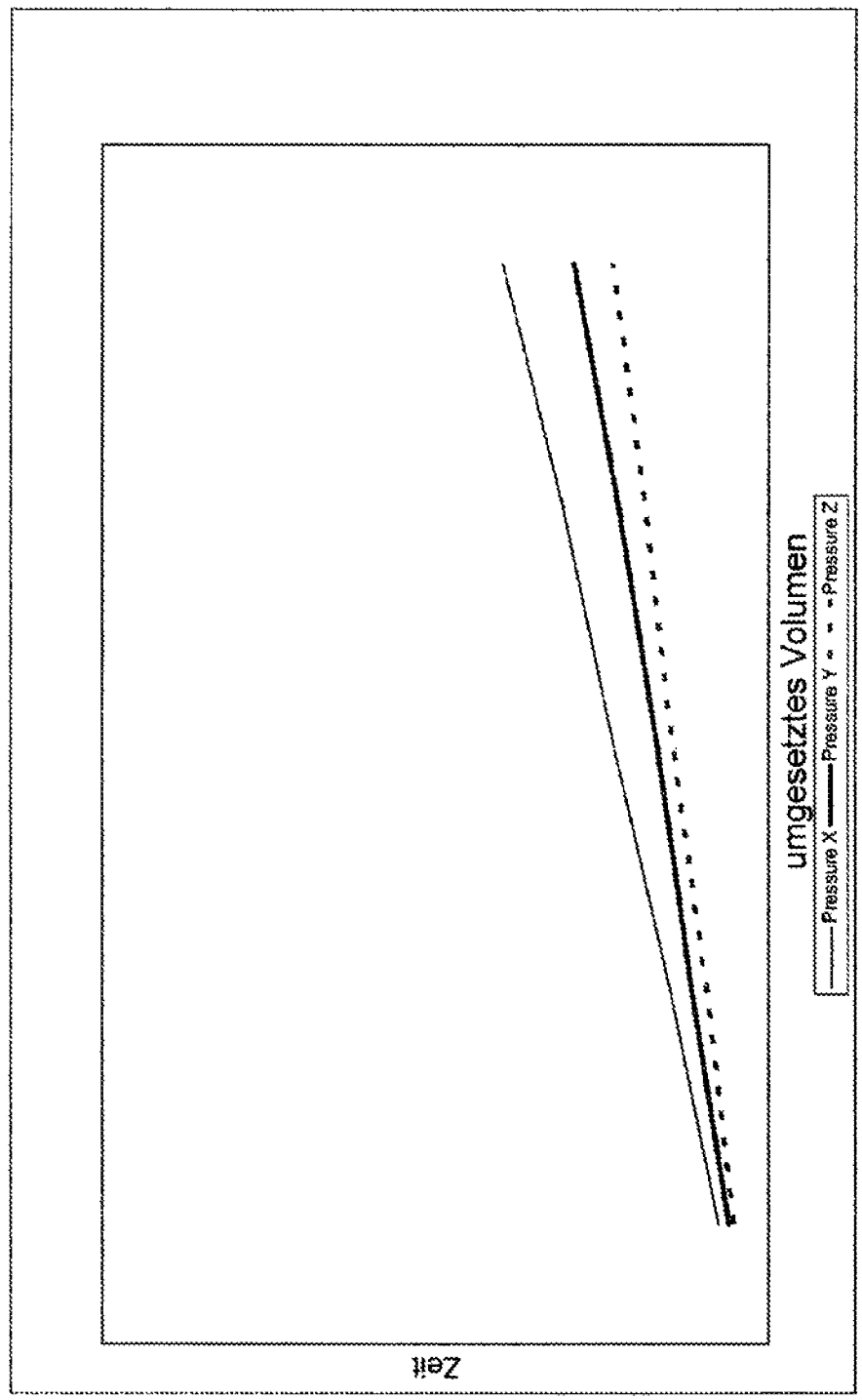
FIG. 9f shows a graph of the volumetric values measured when using different vacuums.

Thus, in the measurement shown in FIG. 9c, four different wound dressings were used in succession, but with the same test liquid and the same suction sequence. In FIG. 9d, with the same wound dressing and suction sequence, four different test liquids were supplied in succession. In FIG. 9e, with the same wound dressing and the same test liquid, different suction sequences were used. In FIG. 9f, another wound dressing was used, but with the same test liquid. Here too, the suction frequency was varied.

Figure 11B:
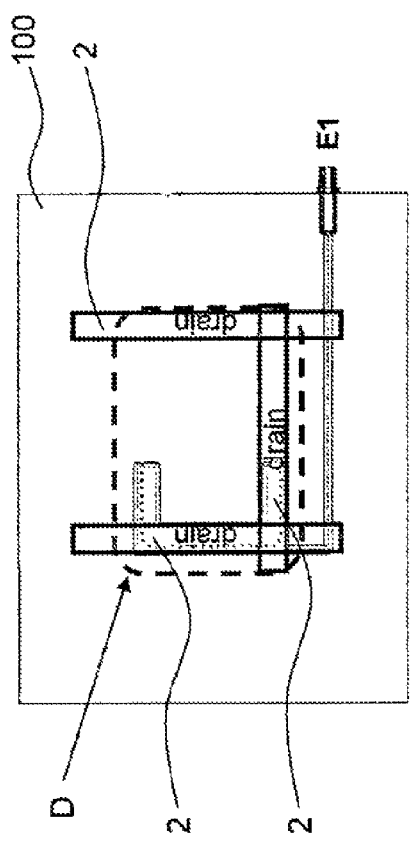
FIG. 11b shows a graph of the measured volumetric values of the sixth application.
Figure 11A:
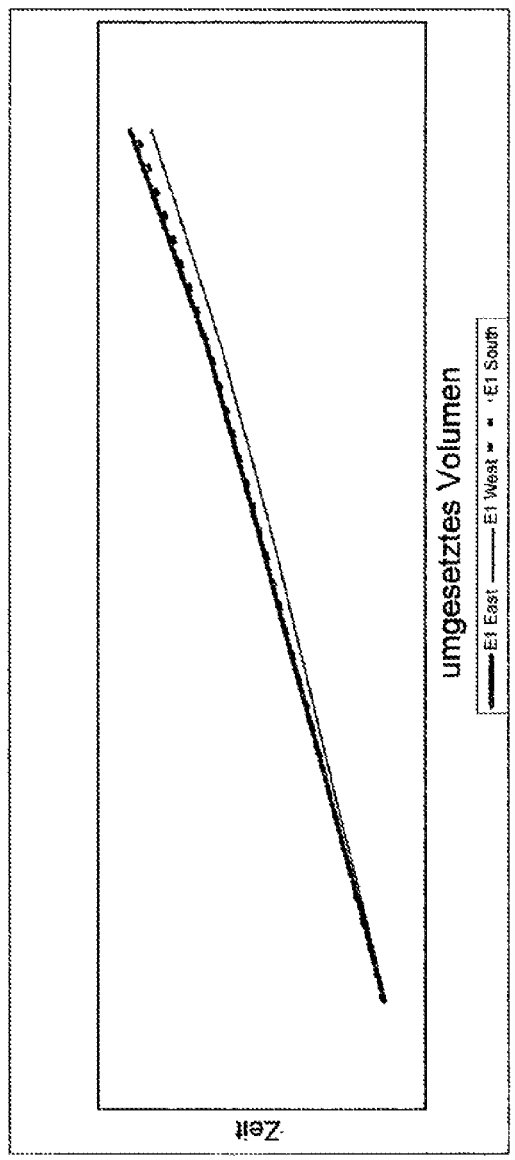
FIG. 11a shows a view of the test unit in a sixth application.
Figure 12B:
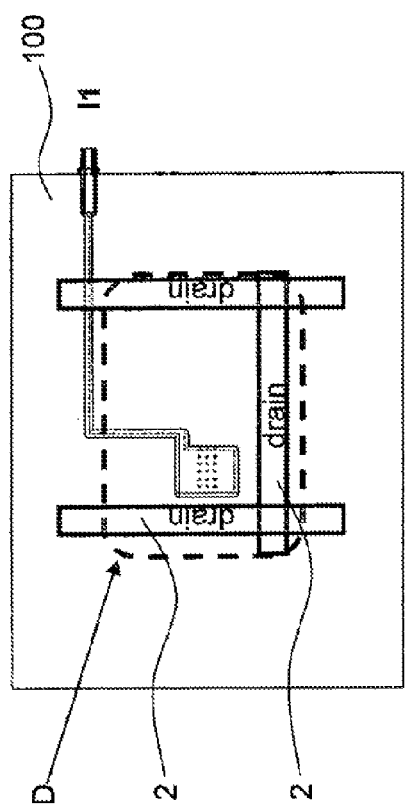
FIG. 12b shows a graph of the measured volumetric values of the seventh application.
Figure 12A:
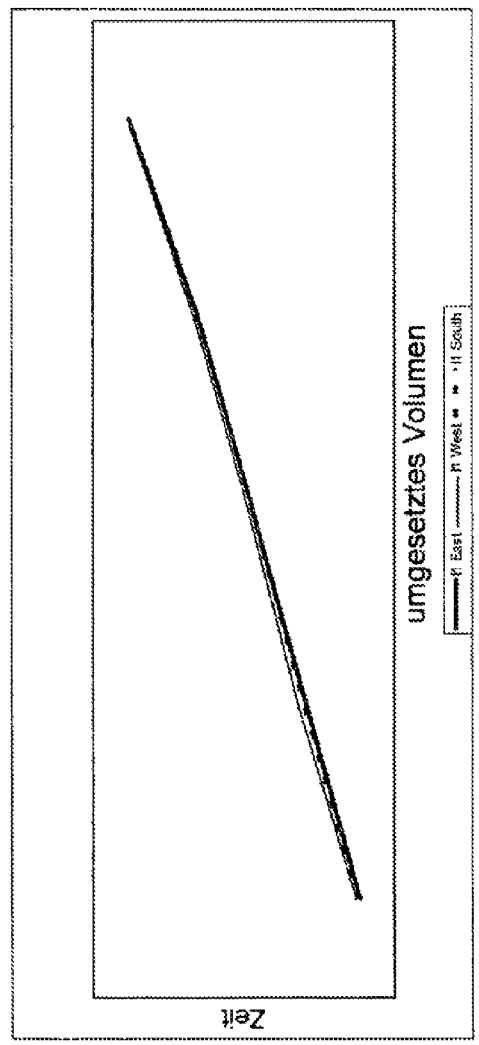
FIG. 12a shows a view of the test unit in a seventh application.
Figure 13B:
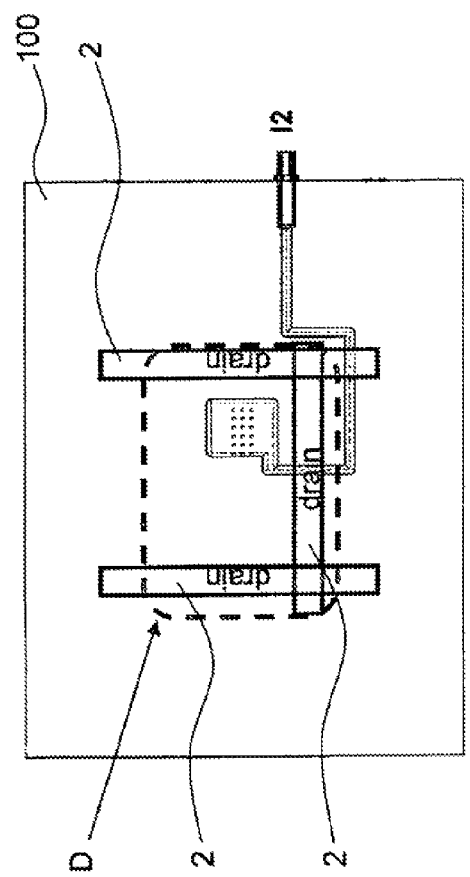
FIG. 13b shows a graph of the measured volumetric values of the eighth application.
Figure 13A:
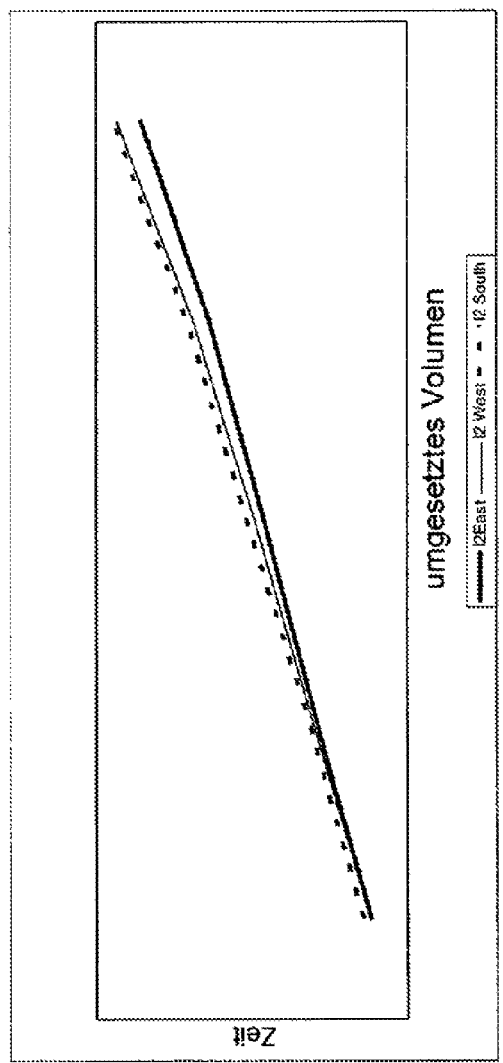
FIG. 13a shows a view of the test unit in an eighth application.

FIGS. 10a and 10b show an experiment in which three drains 2 arranged at different sites were used in succession, but always the same cavity. FIGS. 11a and 11b show the experiment using a different cavity than in the abovementioned example. The same applies to FIGS. 12a and 12b and FIGS. 13a and 13b.

In FIG. 14a, the drain 2 is arranged underneath the wound dressing D. It is arranged inside the wound dressing D in FIG.

14b and above the wound dressing D in FIG. 14c. The measured results are shown in FIG. 14d.

Differently configured drains 2 are used in FIGS. 15a to 15c. The measurement result is shown in turn in FIG. 15d.

As will be seen from these examples, wound drainage applications can be tested in a wide variety of ways by simple and inexpensive means.

The invention claimed is:

1. A test system for wound drainage dressings having a test unit, the test unit comprising:
   a main body with at least one cavity,
   at least one supply line, which runs within the main body and which connects an outer face of the main body to the at least one cavity,
   a support on the surface of the main body arranged over the at least one cavity, for supporting wound dressings and wound drainage covers, and
   a plurality of channels, which run within the main body and which connect the at least one cavity to the support surface, leading from the at least one cavity outward to the support surface,
   wherein a vacuum is able to be generated in the at least one cavity and the channels when the support surface is covered in an airtight manner, and wherein the test system further comprises at least one liquid reservoir, which is able to be connected to the at least one supply line, and a drainage container, which is able to be connected to the support surface via a drainage line and a vacuum attachment.

2. The test system as claimed in claim 1, wherein the main body has a plurality of cavities, which are connected to at least one outer face of the main body via mutually separate supply lines.

3. The test system as claimed in claim 1, wherein the support surface is flat.

4. The test system as claimed in claim 1, wherein the main body has a plurality of cavities which have different volumes.

5. The test system as claimed in claim 1, wherein the channels extend in straight lines in the main body.

6. The test system as claimed in claim 1, wherein the channels have a constant internal diameter.

7. The test system as claimed in claim 1, wherein the channels assigned to a common cavity have the same internal diameter.

8. The test system as claimed in claim 1, wherein the main body has a plurality of cavities and where channels of a common cavity of the plurality of cavities have a different internal diameter than the channels of another cavity of the plurality of cavities.

9. The test system as claimed in claim 1, wherein the main body has a base plate, a supply plate and, a sealing plate between the base plate and the supply plate,
   wherein the base plate has a plane-parallel configuration and
   wherein the supply plate has:
      the at least one supply line,
      at least one recess for forming the at least one cavity, and
      the channels.

10. The test system as claimed in claim 1, wherein the at least one supply line runs in a plane perpendicular to the channels.

11. The test system as claimed in claim 1, wherein a plurality of supply lines open into a common end face of the main body.

12. The test system as claimed in claim 1, wherein a vacuum attachment is present, which is able to be applied over the support surface.

13. The test system as claimed in claim 1, further comprising a suction pump.

14. The test system as claimed in claim 1, further comprising an electronic control and evaluation unit.

* * * * *